United States Patent
Dougherty

Patent Number: 6,127,565
Date of Patent: Oct. 3, 2000

[54] AROMATIC SILANE ETHER-CONTAINING COATINGS

[75] Inventor: T. Kirk Dougherty, Playa Del Rey, Calif.

[73] Assignee: Raytheon Company, Lexington, Mass.

[21] Appl. No.: 09/206,125

[22] Filed: Dec. 4, 1998

[51] Int. Cl.⁷ .................. C07F 7/02; C07F 7/08
[52] U.S. Cl. ............ 556/431; 528/18; 528/21; 528/35; 556/432; 556/435; 556/447; 556/470; 556/480
[58] Field of Search .................. 528/18, 21, 35; 556/431, 432, 435, 447, 470, 480

[56] References Cited

U.S. PATENT DOCUMENTS

| | | | |
|---|---|---|---|
| 3,013,044 | 12/1961 | Schnabel | 556/447 |
| 4,861,901 | 8/1989 | Lau et al. | 549/215 |
| 4,874,643 | 10/1989 | Oldham et al. | 427/340 |
| 5,527,934 | 6/1996 | Jung et al. | 556/435 |

*Primary Examiner*—Robert Dawson
*Assistant Examiner*—Jeffrey B. Robertson
*Attorney, Agent, or Firm*—Colin M. Raufer; Leonard A. Alkov; Glenn H. Lenzen, Jr.

[57] ABSTRACT

The following class of glycidyl and allyl ethers are found to cure at room temperature much faster than their glycidyl and allyl analogs:

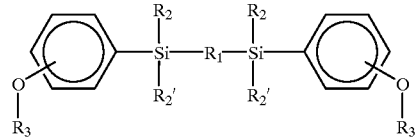

where:

$R_1$ is selected from the group consisting of:
(a) an aliphatic hydrocarbon group containing 2 to 10 carbon atoms; and
(b) a group having the formula

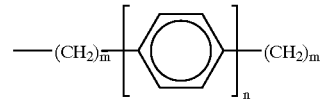

wherein
$n = 1$ to 3,
$m = 0$ to 5
$R_2$ and $R_2'$ are each selected from the group consisting of an alkyl group containing 1 to 4 carbon atoms, an unsubstituted aryl group, and a substituted aryl group, and $R_3$ is selected from the group consisting of

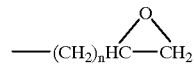

19 Claims, 1 Drawing Sheet

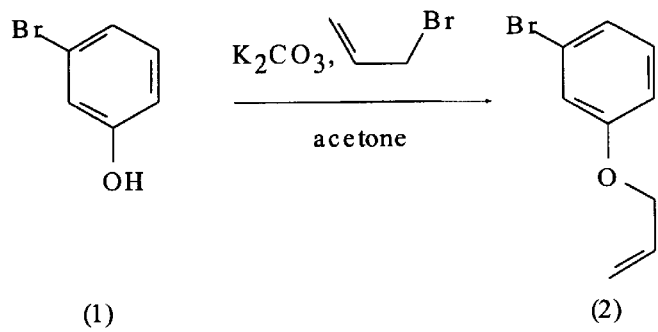
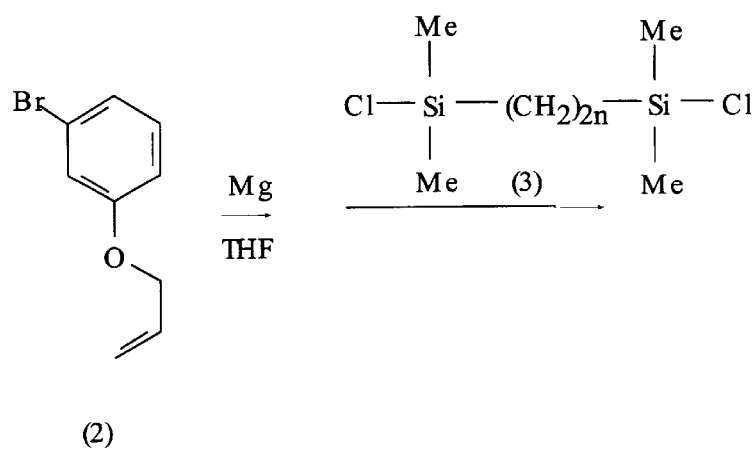
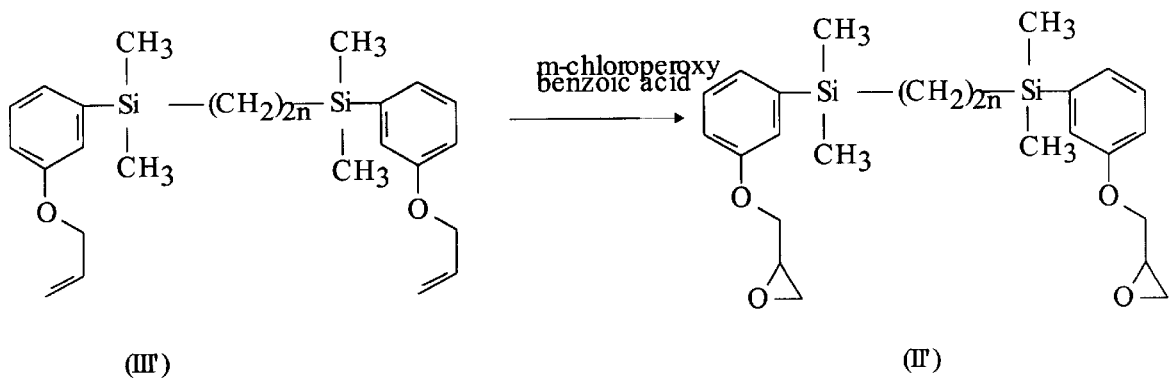

AROMATIC SILANE ETHER-CONTAINING COATINGS

TECHNICAL FIELD

The present invention relates to coating compositions useful as barrier coatings for protecting composite surfaces against physical erosion, such as from rain, plastic media (plastic beads used in a sand-blasting-like operation), and oxygen plasma.

BACKGROUND ART

U.S. Pat. No. 4,874,643, issued on Oct. 17, 1989 to Susan L. Oldham et al and assigned to Hughes Aircraft Company, the teachings of which are incorporated herein by reference, describes a method for rendering a substrate resistant to erosion by a plasma comprising oxygen, and by other erosion phenomenon (for example, rain erosion and plastic media blasting paint removal operations). The erosion resistance is rendered by providing on the surface of the substrate a coating of a cured polymer of a compound having the general formula

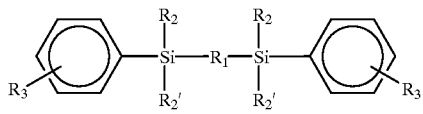

(I)

where:

$R_1$ is selected from the group consisting of:
(a) an aliphatic hydrocarbon group containing 2 to 10 carbon atoms; and
(b) a group having the formula

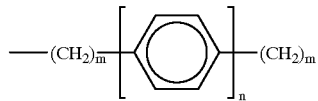

wherein
n=1 to 3,
m=0 to 5,
$R_2$ and $R_2'$ are each selected from the group consisting of an alkyl group containing 1 to 4 carbon atoms, an unsubstituted aryl group, and a substituted aryl group, and $R_3$ comprises

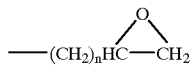

where
n=0 to 10.

U.S. Pat. No. 4,861,901, issued on Aug. 29, 1989, to Kreisler S. Y. Lau et al and also assigned to Hughes Aircraft Company, the teachings of which are incorporated herein by reference, provides an additional $R_3$ moiety, to wit,

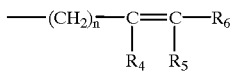

where
$R_4$, $R_5$, and $R_6$ are each selected from the group consisting of H, an alkyl group containing 1 to 4 carbon atoms, and an aryl group, and where
n=0 to 10.

A preferred compound is 1,8-bis(m-glycidylphenyldimethylsilyl)octane or 1,8-octanediylbis (dimethyl(3-(oxiranylmethyl)phenyl)silane; the name given to this compound in the above-identified patents is 2,11-bis (3-glycidylphenyl)-2,11-dimethyl -2,11-disiladodecane (CAS 120390-91-2). Herein, this compound and its analogs will be referred to by the first of the above three names, namely, the octane. In any event, in formula (I) above, $R_1$ is an aliphatic hydrocarbon group containing 8 carbon atoms, $R_2$ and $R_2'$ are each —$CH_3$ and n in $R_3$ is 1. The resulting formula is

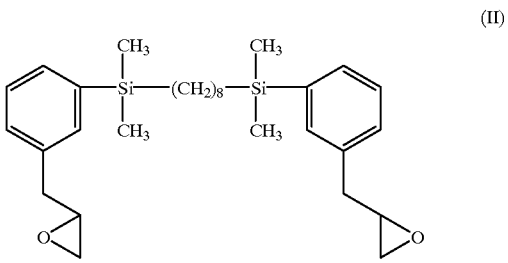

(II)

also called HRG-3.

However, while this patent is suitable for its intended purpose, the present inventor has found that HRG-3 is difficult to formulate into a coating that can be easily cured at room temperature. Even when formulated with very reactive epoxy diluents and amine curing agents, full cure occurs at room temperature only after 72 hours. In addition, one of the synthetic intermediates, 3-allylbromobenzene, is difficult to make and employs expensive starting materials. Yields have been found to be low and difficult to improve for this intermediate. Also, this intermediate material is very difficult to purify.

Thus, what is needed is an erosion-resistant coating that employs a less expensive intermediate, is easier to prepare, and cures at room temperature in a matter of hours, not days, while retaining most, if not all, of the advantages of the prior art coating.

DISCLOSURE OF INVENTION

In accordance with the present invention, the above glycidyl- and allyl-containing compounds are prepared as glycidyl ethers and allyl ethers, respectively, in which —$R_3$ is replaced with —O—$R_3$; the glycidyl (and allyl) ethers cure much faster than their glycidyl (and allyl) analogs. The teachings of the present invention provide glycidyl ether- and allyl ether-containing coatings which use a less expensive and easier to prepare starting material. These new compositions of matter, when formulated and cured with available epoxy curing agents, cure at room temperature in several hours (not days) and gives a protective coating material with properties equivalent or superior to the coatings of the cited reference. Since the coatings of the present invention cure much faster as compared to the coatings of the cited reference, recoating or rework can occur after only hours and final superior material properties occur in a cycle time considerably less than that disclosed in the prior art.

The glycidyl ether and allyl ether compounds of the present invention form barrier coatings that are suitable for protecting, e.g., composite surfaces against physical erosion, such as from rain, plastic media (plastic beads), and oxygen plasma.

BRIEF DESCRIPTION OF THE DRAWING

The sole FIGURE depicts the reaction sequence for forming a preferred compound, 2,8-bis(3-glycidyloxyphenyldimethylsilyl)octane, given by formula (II') below.

BEST MODES FOR CARRYING OUT THE INVENTION

In accordance with the present invention, a substrate is rendered resistant to erosion by forming on the surface of the substrate a coating of a cured polymer of a compound having the general formula

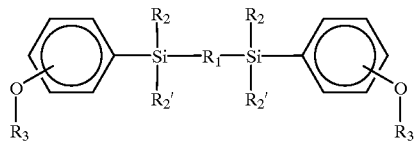

(I')

where:

R$_1$ is selected from the group consisting of:
(a) an aliphatic hydrocarbon group containing 2 to 10 carbon atoms; and
(b) a group having the formula

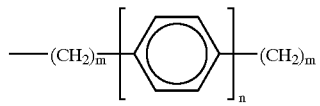

wherein n=1 to 3, m=0 to 5

R$_2$ and R$_2'$ are each selected from the group consisting of an alkyl group containing 1 to 4 carbon atoms, an unsubstituted aryl group, and a substituted aryl group, and R$_3$ is selected from the group consisting of

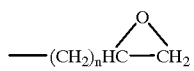

and

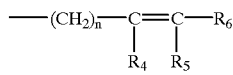

where

R$_4$, R$_5$, and R$_6$ are each selected from the group consisting of H, an alkyl group containing 1 to 4 carbon atoms, and an aryl group, and where n=1 to 10.

A preferred compound is given by the formula

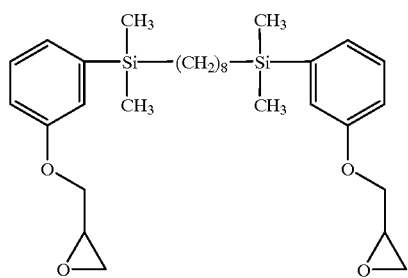

(II')

The difference between formulae (I) and (I') and between formulae (II) and (II') is the presence of the ether linkage in formulae (I') and (II'). That ether linkage, however, is key to reducing the curing time at room temperature substantially from days to several hours.

Referring now to the Figure, the glycidyl ether of formula (I') is formed by the following reaction sequence, with reference to the specific formation of formula (II'):

1. m-Bromophenol (1) is reacted with allylbromide in the presence of potassium carbonate and acetone to form 3-bromophenylallyl ether (2).

2. 3-Bromophenylallyl ether (2) is reacted with magnesium in tetrahydrofuran and then 2,8-bis(chlorodimethylsilyl)octane (3) (n=4) is added to form 2,8-bis (3-allyloxyphenyldimethylsilyl)octane (III') (n=4).

3. 2,8-bis(3-allyloxyphenyldimethylsilyl)octane (III') is reacted with m-chloroperoxybenzoic acid to form the final product, 2,8-bis (3-glycidyloxyphenyldimethylsilyl octane (II').

While the reaction sequence is depicted for a specific final product, it will be appreciated, based on the teachings of the above-referenced patents, that other compounds encompassed by formula (I) may be similarly prepared.

Another preferred compound is 2,8-bis(3-allyloxyphenyldimethylsilyl)octane, given by the formula (III'):

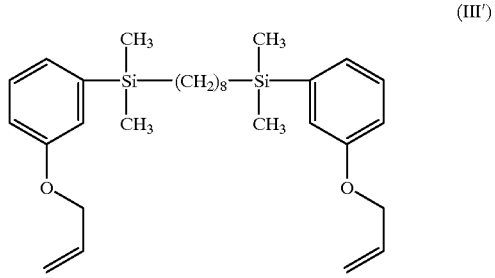

(III')

Compound (III') with the allylic ether moiety is useful for forming homo-polymers and copolymers for application as low dielectric materials.

Polymerization of compounds encompassed by Formula (I') above may be performed, using known curing agents, such as 1,3-bis(3-aminopropyl)-1,1,3,3-tetramethyl-1,3-disiloxane (APMD), 1,3-bis(3-aminobutyl)-1,1,3,3-tetramethyl-1,3-disiloxane (ABMD), triethylenetetraamine, m-phenylenediamine, 4,4'-methylenedianiline, diaminodiphenylsulfone, nadic methylanhydride, methyltetrahydride, and 2-ethyl -4-methylimidazole, or other amine, amide, acid, and nitrogen-containing agents to form the polymer. Also, the epoxy monomer may be copolymerized with commercially-avail-able epoxy materials, such as DGEBA (the diglycidyl ether of Bisphenol A, available from Shell Chemical), of which EPON 825 is an industry standard, epoxy phenol novalacs (such as DEN 438, available from Dow Chemical), epoxy cresol novalacs (such as ECN 1235, available from Ciba Geigy), and tetraglycidylmethylene dianilines (such as MY 720, available from Ciba Geigy), to improve the compliance (ability of an object to yield elastically when a force is applied).

Further, the epoxy monomers of the present invention may be reacted with an amine functionalized compound to form an amine adduct. Examples of suitable amine functionalized compounds include ethylenediamine and aminoethylpiperazine.

As an example, the reaction of (II') with ethylenediamine provides the following low viscosity amine adduct, which is the ether analog of a low viscosity amine adduct that is the subject of a related patent application, Ser. No. 09/015,112, filed on Jan. 29, 1998:

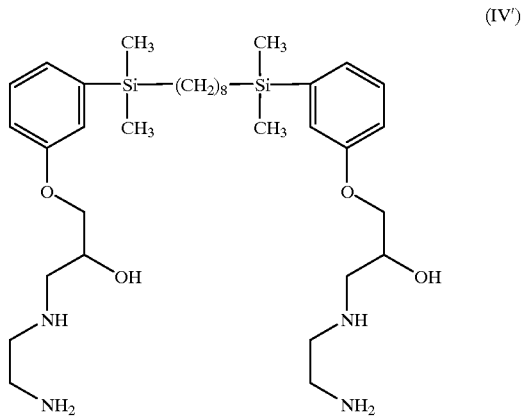

(IV')

Coatings of the above polymers, formed to a thickness in the range of about 0.001 to 0.020 inch (about 0.0025 to 0.051 cm) on a substrate, are resistant, for example, to erosion by rain, plastic media, and an oxygen plasma, including elemental oxygen.

EXAMPLES

Preparation of 3-bromophenylallyl ether: A well-stirred mixture of 3-bromophenol (348.2 g, 2.0 mole), allylbromide (278 g, 2.29 mole) and dry acetone (500 g) was heated to a gentle reflux. Anhydrous potassium carbonate (300 g, 2.17 mole) was added over a period of 3 hours. Care was taken to insure a gentle evolution of carbon dioxide during the addition of the base. The reaction mixture was cooled, filtered and concentrated on a rotary evaporator. The crude product was purified by vacuum distillation to give a small forerun (10.2 g) and then 383.5 g of the product, 3-bromophenyallyl ether (b.p. 82° C. at 1.5 Torr, 99.5% pure by gas chromatography). This is an 89% conversion yield, based on the limiting reagent, 3-bromophenol.

$^{13}$C NMR (50.2 MHz, CDCl$_3$): 159.27, 132.64, 130.45, 123.85, 122.69, 117.92, 117.87, 113.66, 68.86.

$^1$HNMR (200 MHz, CDCl$_3$): 7.1–6.9 (m, 3H, aromatic), 6.7–6.6 (m, 1H, aromatic), 6.05–5.81 (m, 1H, allylic), 5.38–5.1 (m, 2H, allylic), 4.44–4.36 (m, 2H aliphatic).

Preparation of 2,8-bis(3-allyloxyphenyl) dimethylsilyloctane: To a well stirred mixture of dry magnesium turnings (2.4 g, 0.1 mole) in 15 mL of dry tetrahydrofuran was added 3-bromophenylallyl ether (21.3 g, 0.1 mole). An exothermic reaction immediately took place. After complete addition, the contents were stirred and refluxed an additional hour. Bis(chlorodimethylsilyl) octane (13.7 g, 0.045 mole) was added to the formed Grignard over a period of 30 min, and the mixture was refluxed an additional hour. After cooling, the mixture was poured into 100 mL of an ammonium chloride solution and the aqueous washing extracted with 2×50 mL of hexane. The combined organic solutions were washed with saturated sodium chloride solution, dried over anhydrous magnesium sulfate, filtered, and concentrated on a rotary evaporator to give the product (20.2 gram, 91% yield). Gas chromatography analysis of the material was not successful, no doubt due to Claissen rearrangement of the product in the chromatograph. NMR analysis was used to identify the product.

$^{13}$C NMR (50.2 MHz, CDCl$_3$): 157.89, 141.42, 133.28, 128.82, 125.95, 120.04, 117.63, 114.50, 68.62, 33.60, 29.21, 23.80, 15.62, -3.04.

$^1$H NMR (200 MHz, CDCl$_3$): 7.3–6.7 (m, 8H, aromatic), 6.15–5.91(M, 2H, allylic), 5.4–5.1(m, 4H, allylic), 4.54 (m, 4H, aliphatic), 1.25(brd s, 12H, aliphatic), 0.63(m, 4H, aliphatic-Si), 0.22(s, 12H, Si—Me).

Preparation of 2,8-bis(3-glycidyloxyphenyldimethylsilyl) octane: The above-described bis-allylether (2.5 grams, 0.005 mole) was dissolved in 30 mL of chloroform. To this mixture was added 3-chloroperbenzoic acid (60% active oxygen, 2.5 grams, 0.008 mole). The 3-chloroperbenzoic acid was very wet and the reaction mixture was immediately dried over anhydrous sodium sulfate and decanted. The reaction mixture was stirred for 2 hours at 50° C., cooled, and the contents filtered and the solid washed with a small amount of chloroform. The liquid was allowed to stir an additional two hours, filtered again and stirred overnight. The idea here was to keep contact between the epoxy product and the acidic byproduct (3-chlorobenzoic acid) and water to a minimum. Both the silicon phenyl bond and the epoxide are susceptible to electrophilic attack.

The next day, a small amount of the mixture was evaporated and the chloroform soluble portion analyzed by NMR. The epoxidation was judged about 40% complete. An additional 2.5 grams of the per acid was added and dried as above. The mixture was stirred at room temperature for 3 hours, the slurry was filtered, evaporated and the hexane soluble portion was filtered and evaporated to give the crude product 1.5 grams (56% of theory).

$^1$H NMR (200 MHz, CDCl$_3$): 7.3–6.7 (m, 8H, aromatic), 4.2 (m, 2H), 4.05(m, 2H), 3.35(m, 2H), 2.9(m, 2H) 2.7(m, 2H) (this is nearly identical to the characteristic aromatic glycidyl ether of Epon 828), 1.25(brd s, 12H, aliphatic), 0.63(m, 4H, aliphatic-Si), 0.22(s, 12H, Si—Me).

Curing of the glycidyl ethers of the present invention is performed using amines or amine adducts, and, due to the presence of the ether oxygen linkage, is expected to take about 4 to 12 hours at room temperature. Coatings on substrates evidence the same or better erosion protection properties as formula (I).

Thus, there has been disclosed a composition of matter giving physical properties comparable to HRG-3 resin that can by synthesized in higher yield and using lower cost starting materials than the prior art. The use of this glycidyl ether allows much faster cure than the prior art. The use of 3-bromophenylallyl ether in this scheme as compared to 3-bromoallylbenzene of the prior art provides for a higher yield and lower cost synthetic process.

What is claimed is:

1. A compound having the formula

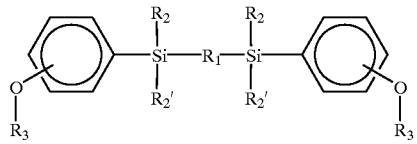

where:

$R_1$ is selected from the group consisting of:
(a) an aliphatic hydrocarbon group containing 2 to 10 carbon atoms; and
(b) a group having the formula

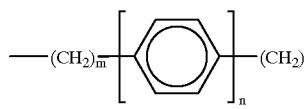

wherein n=1 to 3, m=0 to 5

$R_2$ and $R_2'$ are each selected from the group consisting of an alkyl group containing 1 to 4 carbon atoms, an unsubstituted aryl group, and a substituted aryl group, and $R_3$ is selected from the group consisting of

and

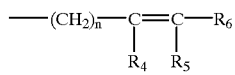

where $R_4$, $R_5$, and $R_6$ are each selected from the group consisting of H, an alkyl group containing 1 to 4 carbon atoms, and an aryl group, and where n=1 to 10.

2. The compound of claim 1 wherein $R_1$ is an aliphatic hydrocarbon group containing 8 carbon atoms, $R_2$ and $R_2'$ are each —CH$_3$ and $R_3$ is an epoxide having the structure

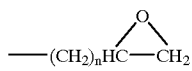

where n=1.

3. The compound of claim 2 having the formula

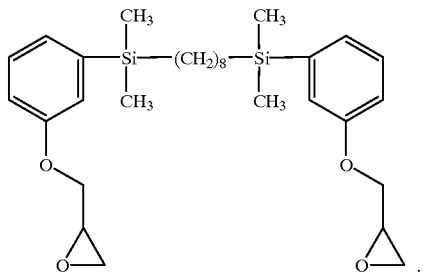

4. The compound of claim 1 wherein $R_1$ is an aliphatic hydrocarbon group containing 8 carbon atoms, $R_2$ and $R_2'$ are each —CH$_3$ and $R_3$ is —CH$_2$—CH=CH$_2$.

5. The compound of claim 4 having the formula

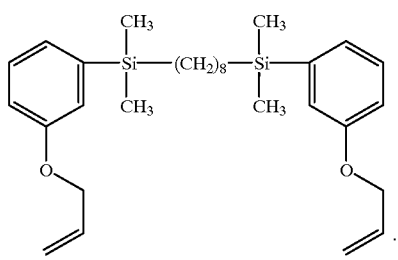

6. An amine adduct of the compound of claim 1, wherein $R_3$ is an epoxide having the structure

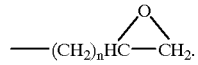

7. The amine adduct of claim 6 formed by the reaction of the epoxide with an amine functionalized compound selected from the group consisting of ethylenediamine and aminoethylpiperazine.

8. An amine adduct of the compound of claim 2.

9. The amine adduct of claim 8 formed by the reaction of the epoxide with an amine functionalized compound selected from the group consisting of ethylenediamine and aminoethylpiperazine.

10. A method for rendering a surface of a substrate resistant to erosion, said method comprising forming on said surface of said substrate a coating of a cured polymer of a compound having the formula

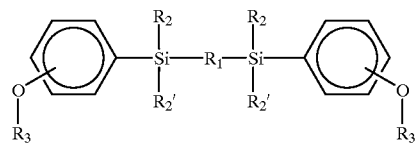

where:

$R_1$ is selected from the group consisting of:
(a) an aliphatic hydrocarbon group containing 2 to 10 carbon atoms; and (b) a group having the formula

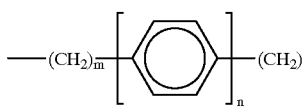

wherein n=1 to 3, m=0 to 5

$R_2$ and $R_2'$ are each selected from the group consisting of an alkyl group containing 1 to 4 carbon atoms, an unsubstituted aryl group, and a substituted aryl group, and $R_3$ is selected from the group consisting of

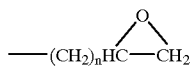

and

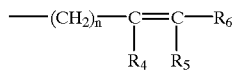

where $R_4$, $R_5$, and $R_6$ are each selected from the group consisting of H, an alkyl group containing 1 to 4 carbon atoms, and an aryl group, and where n=1 to 10.

11. The method of claim 10 wherein $R_1$ is an aliphatic hydrocarbon group containing 8 carbon atoms, $R_2$ and $R_2'$ are each —$CH_3$ and $R_3$ is

where n=1.

12. The method of claim 11 wherein said compound is given by the formula

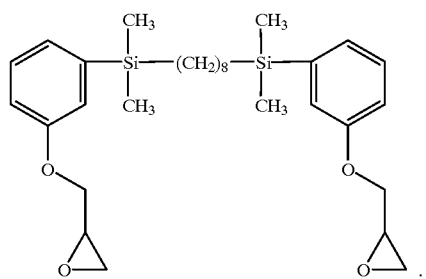

13. The method of claim 10 wherein $R_1$ is an aliphatic hydrocarbon group containing 8 carbon atoms, $R_2$ and $R_2'$ are each —$CH_3$ and $R_3$ is —$CH_2$—$CH_2$—$CH$=$CH_2$.

14. The method of claim 13 wherein said compound is given by the formula

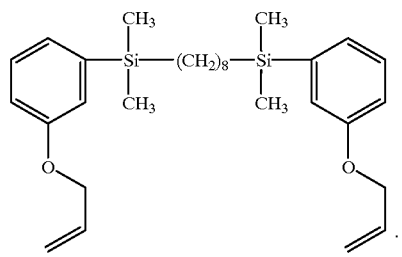

15. A method for increasing the cure rate at room temperature of a compound having the formula

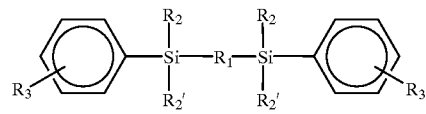

where:

$R_1$ is selected from the group consisting of:
(a) an aliphatic hydrocarbon group containing 2 to 10 carbon atoms; and
(b) a group having the formula

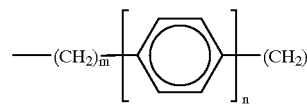

wherein n=1 to 3, m=0 to 5

$R_2$ and $R_2'$ are each selected from the group consisting of an alkyl group containing 1 to 4 carbon atoms, an unsubstituted aryl group, and a substituted aryl group, and $R_3$ is selected from the group consisting of

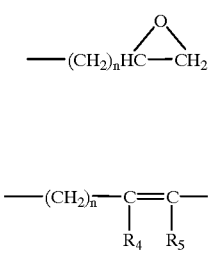

and

where $R_4$, $R_5$, and $R_6$ are each selected from the group consisting of H, an alkyl group containing 1 to 4 carbon atoms, and an aryl group, and where n=1 to 10, said method comprising replacing said $R_3$ with —O—$R_3$ to form a glycidyl ether or an allyl ether, respectively.

16. The method of claim 15 wherein $R_1$ is an aliphatic hydrocarbon group containing 8 carbon atoms, $R_2$ and $R_2'$ are each —$CH_3$ and $R_3$ is

where n=1 to form said glycidyl ether.

17. The method of claim 16 wherein said glycidyl ether is given by the formula

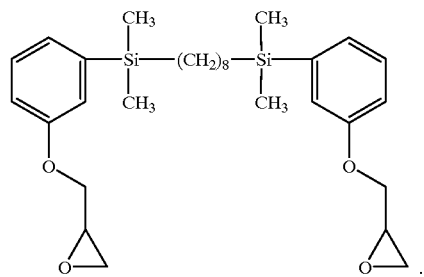

18. The method of claim 15 wherein $R_1$ is an aliphatic hydrocarbon group containing 8 carbon atoms, $R_2$ and $R_2'$ are each —$CH_3$ and $R_3$ is —$CH_2$—$CH$=$CH_2$ to form said allyl ether.

19. The method of claim 18 wherein said allyl ether is given by the formula

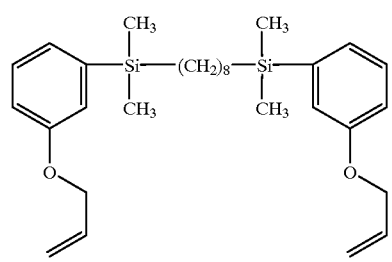

and

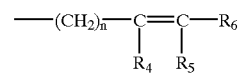

where $R_4$, $R_5$, and $R_6$ are each selected from the group consisting of H, an alkyl group containing 1 to 4 carbon atoms, and an aryl group, and where n=1 to 10.

* * * * *